United States Patent [19]
Mililli et al.

[11] Patent Number: 5,680,981
[45] Date of Patent: Oct. 28, 1997

[54] SELF-CONTAINED POWERED SURGICAL APPARATUS

[75] Inventors: Carlo A. Mililli, Huntington, Conn.; Wayne P. Young, Brewster, N.Y.; Stephan A. DeFonzo; Dominick L. Mastri, both of Bridgeport, Conn.; Henry Bolanos, East Norwalk; Leonard Stern, Southington, both of Conn.

[73] Assignee: United States Surgical Corporation, Norwalk, Conn.

[21] Appl. No.: 643,395

[22] Filed: May 6, 1996

Related U.S. Application Data

[63] Continuation of Ser. No. 238,770, May 5, 1994, abandoned.
[51] Int. Cl.$^6$ ............................................. A61B 17/068
[52] U.S. Cl. ........................ 227/175.1; 227/19; 227/176.1
[58] Field of Search ................................ 227/19, 175.1, 227/176.1, 178.1

[56] References Cited

U.S. PATENT DOCUMENTS

| | | |
|---|---|---|
| 1,881,250 | 10/1932 | Tomlinson . |
| 2,905,178 | 9/1959 | Hilzinger, III . |
| 3,618,842 | 11/1971 | Bryan . |
| 3,815,476 | 6/1974 | Green et al. . |
| 3,952,748 | 4/1976 | Kaliher et al. . |
| 4,071,029 | 1/1978 | Richmond et al. . |
| 4,289,131 | 9/1981 | Mueller . |
| 4,334,539 | 6/1982 | Childs et al. . |
| 4,484,503 | 11/1984 | Sitte et al. . |
| 4,489,724 | 12/1984 | Arnegger . |
| 4,494,057 | 1/1985 | Hotta . |
| 4,605,001 | 8/1986 | Rothfuss et al. . |
| 4,644,952 | 2/1987 | Patipa et al. . |
| 4,650,460 | 3/1987 | Roizenblatt . |
| 4,655,673 | 4/1987 | Hawkes . |
| 4,662,555 | 5/1987 | Thornton . |
| 4,664,305 | 5/1987 | Blake, III et al. . |
| 4,705,038 | 11/1987 | Sjostrom et al. . |
| 4,733,118 | 3/1988 | Mihalko . |
| 4,771,774 | 9/1988 | Simpson et al. . |
| 4,867,158 | 9/1989 | Sugg . |
| 4,887,599 | 12/1989 | Muller . |
| 4,919,152 | 4/1990 | Ger . |
| 4,936,845 | 6/1990 | Stevens . |
| 4,951,860 | 8/1990 | Peters et al. ........................ 227/19 |

(List continued on next page.)

FOREIGN PATENT DOCUMENTS

| | | |
|---|---|---|
| 0041022 | 12/1981 | European Pat. Off. . |
| 0156774 | 10/1985 | European Pat. Off. . |
| 0216532 | 4/1987 | European Pat. Off. . |
| 0399701 | 11/1990 | European Pat. Off. . |
| 0539762 | 5/1993 | European Pat. Off. . |
| 0552050 | 7/1993 | European Pat. Off. . |
| 0592244 | 4/1994 | European Pat. Off. . |
| 0593920 | 4/1994 | European Pat. Off. . |
| 0598579 | 5/1994 | European Pat. Off. . |
| 0621006 | 10/1994 | European Pat. Off. . |
| 0634144 | 1/1995 | European Pat. Off. . |
| 2660851 | 10/1991 | France . |
| 2903159 | 7/1980 | Germany . |
| 3114135 | 10/1982 | Germany . |
| 4213426 | 10/1992 | Germany . |
| 659146 | 4/1979 | U.S.S.R. . |
| 9308754 | 5/1993 | WIPO . |
| 9314706 | 8/1993 | WIPO . |

Primary Examiner—Scott A. Smith

[57] ABSTRACT

A self-contained powered surgical stapling apparatus is provided which includes an elongate body, a fastener applying assembly including an anvil for forming a surgical fastener driven thereagainst, a motor assembly and power source for energizing the motor assembly disposed within the elongate body, and a pusher driven by the motor assembly for driving a surgical fastener toward the anvil to be formed thereby and fastened to body tissue. The apparatus is configured for utilization during conventional invasive surgical procedures as well as endoscopic or laparoscopic surgical procedures by providing a detachable extension shaft.

22 Claims, 14 Drawing Sheets

U.S. PATENT DOCUMENTS

| | | |
|---|---|---|
| 4,995,877 | 2/1991 | Ams et al. . |
| 5,059,203 | 10/1991 | Husted . |
| 5,125,553 | 6/1992 | Oddsen et al. . |
| 5,133,359 | 7/1992 | Kedem . |
| 5,133,713 | 7/1992 | Huang et al. . |
| 5,133,729 | 7/1992 | Sjostrom . |
| 5,170,925 | 12/1992 | Madden et al. . |
| 5,174,487 | 12/1992 | Rothfuss et al. . |
| 5,176,692 | 1/1993 | Wilk et al. . |
| 5,192,292 | 3/1993 | Cezana et al. . |
| 5,201,750 | 4/1993 | Hocherl et al. . |
| 5,207,697 | 5/1993 | Carusillo et al. . |
| 5,221,279 | 6/1993 | Cook et al. . |
| 5,237,884 | 8/1993 | Seto . |
| 5,246,156 | 9/1993 | Rothfuss et al. . |
| 5,249,583 | 10/1993 | Mallaby . |
| 5,258,007 | 11/1993 | Spetzler et al. . |
| 5,261,877 | 11/1993 | Fine et al. . |
| 5,268,622 | 12/1993 | Philipp . |
| 5,289,963 | 3/1994 | McGarry et al. . |
| 5,326,013 | 7/1994 | Green et al. . |
| 5,356,064 | 10/1994 | Green et al. . |
| 5,467,911 | 11/1995 | Tsuruta et al. . |

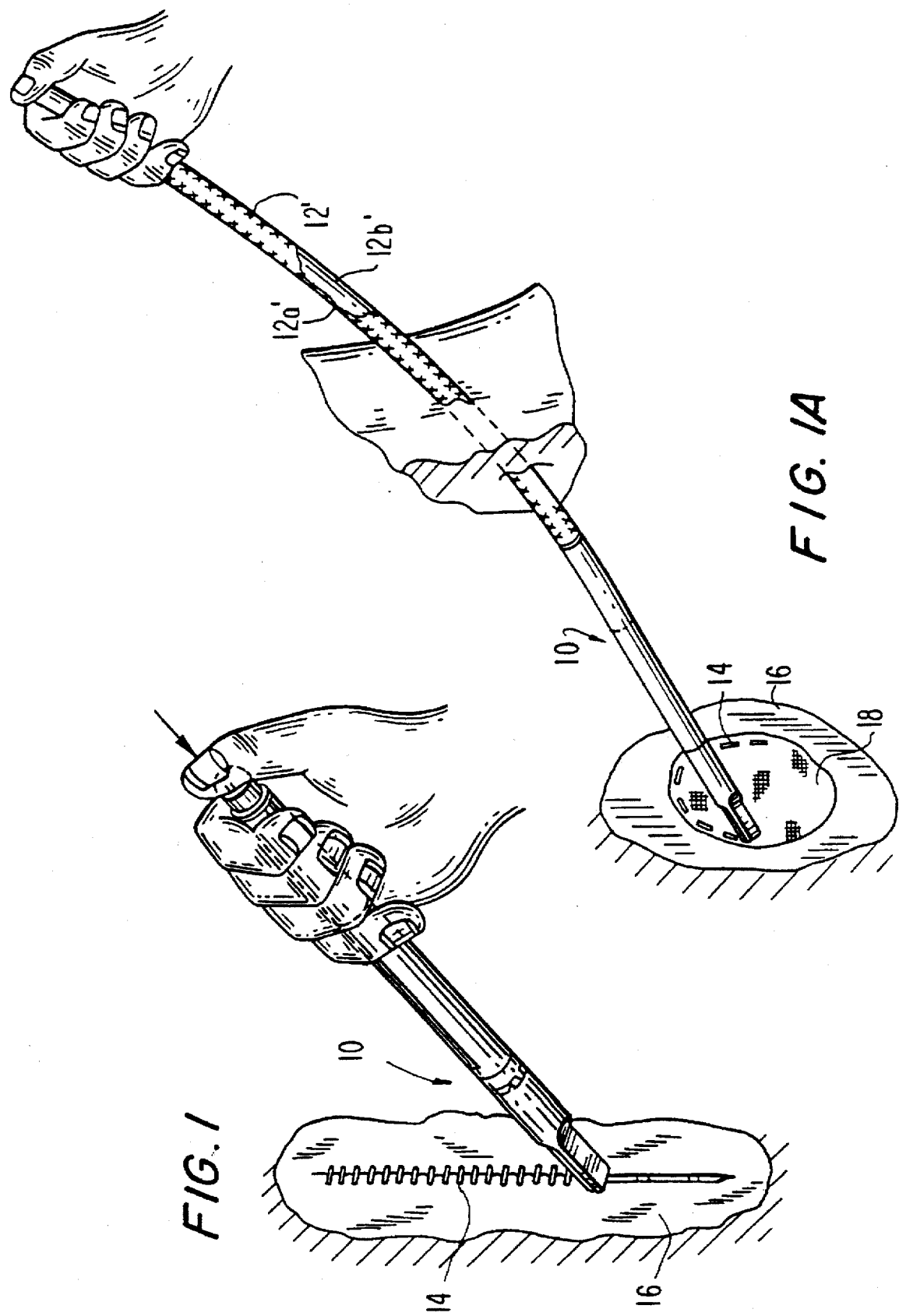

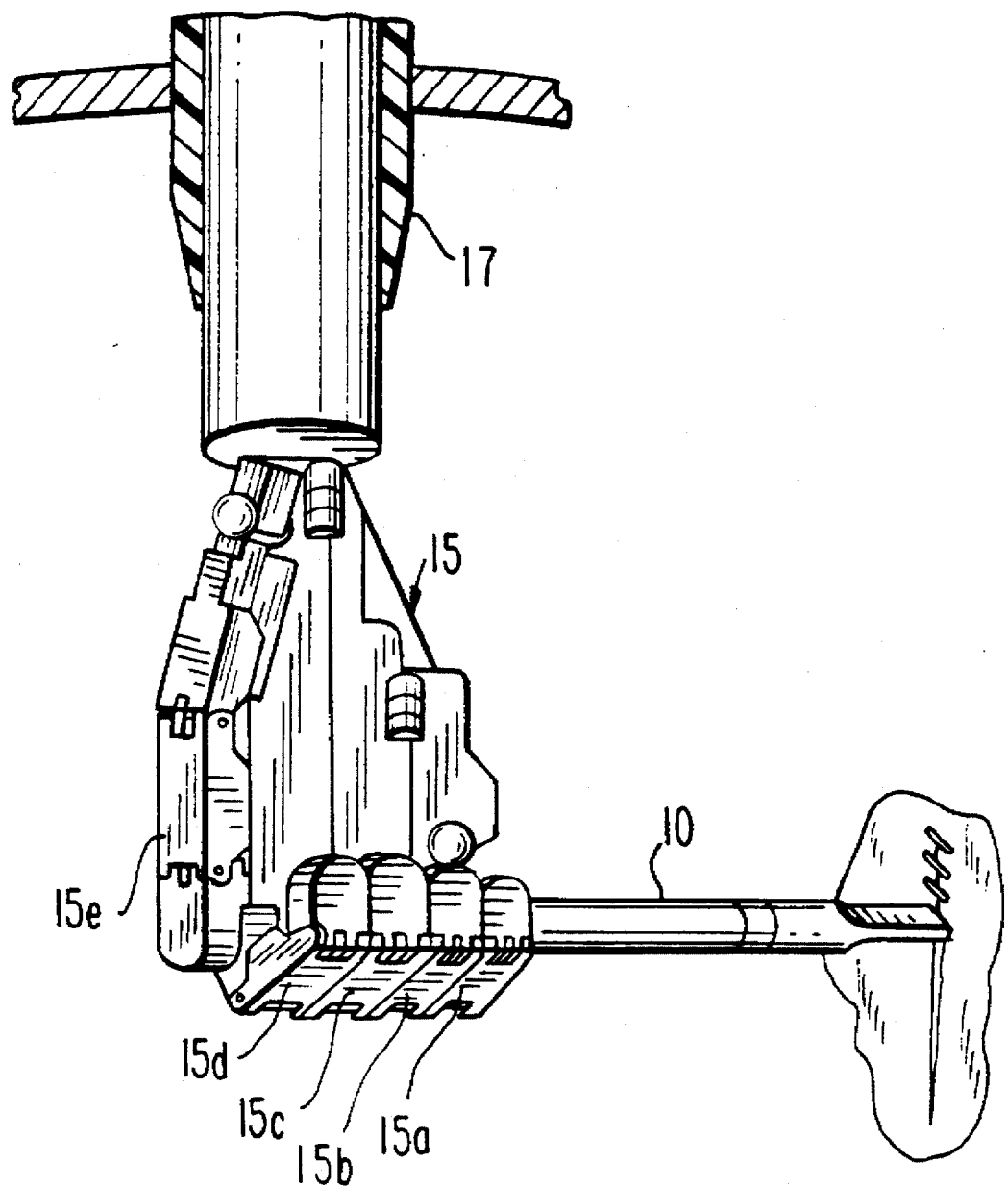
F I G. 2

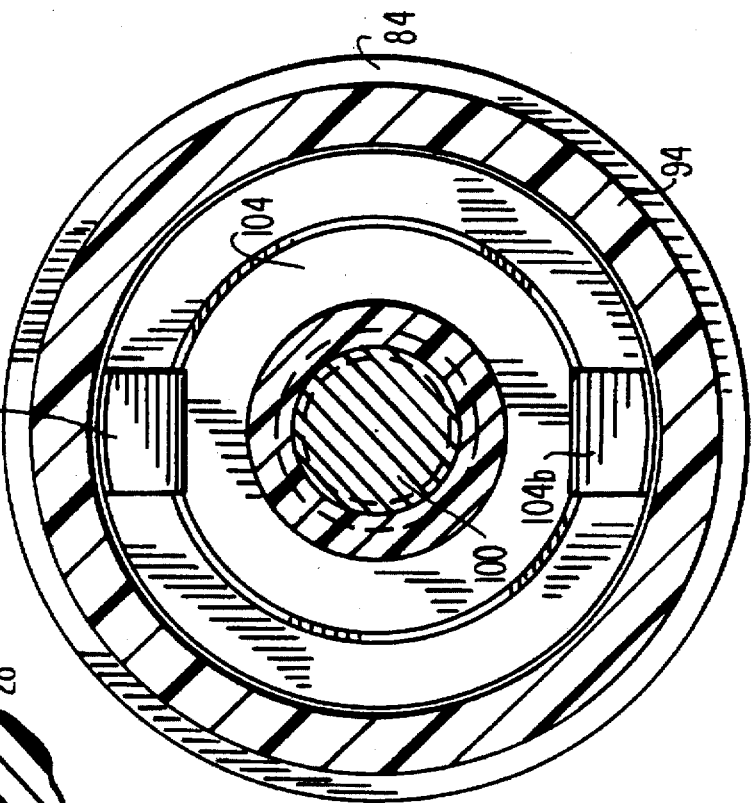
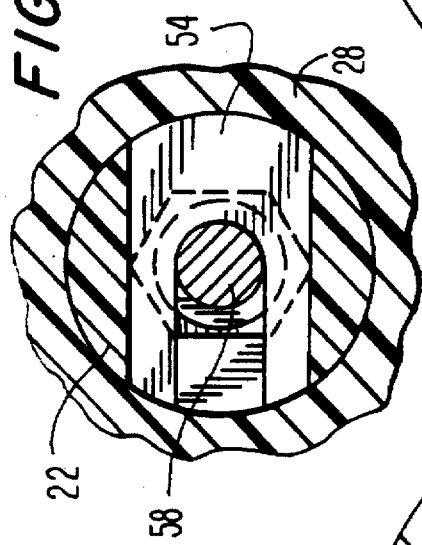
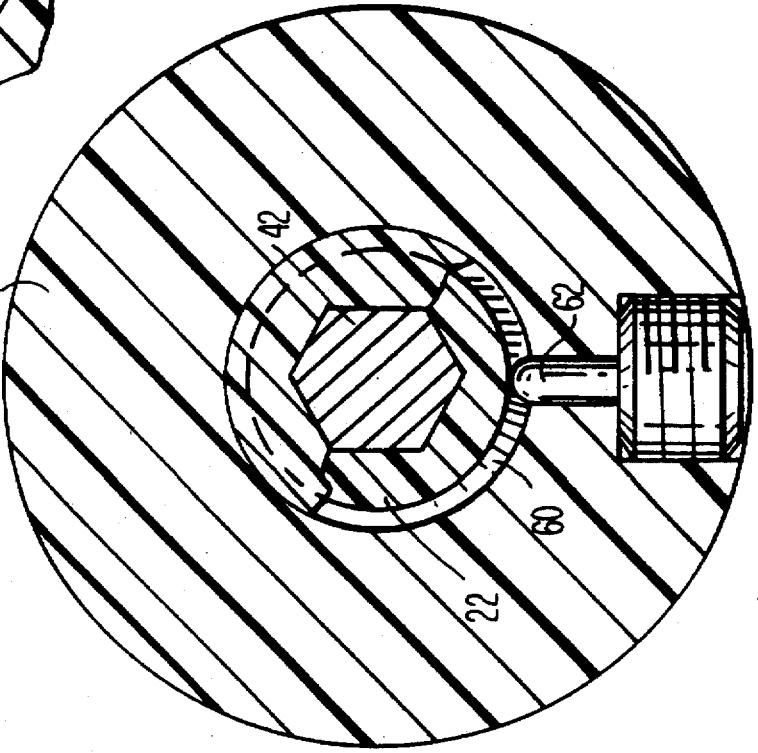

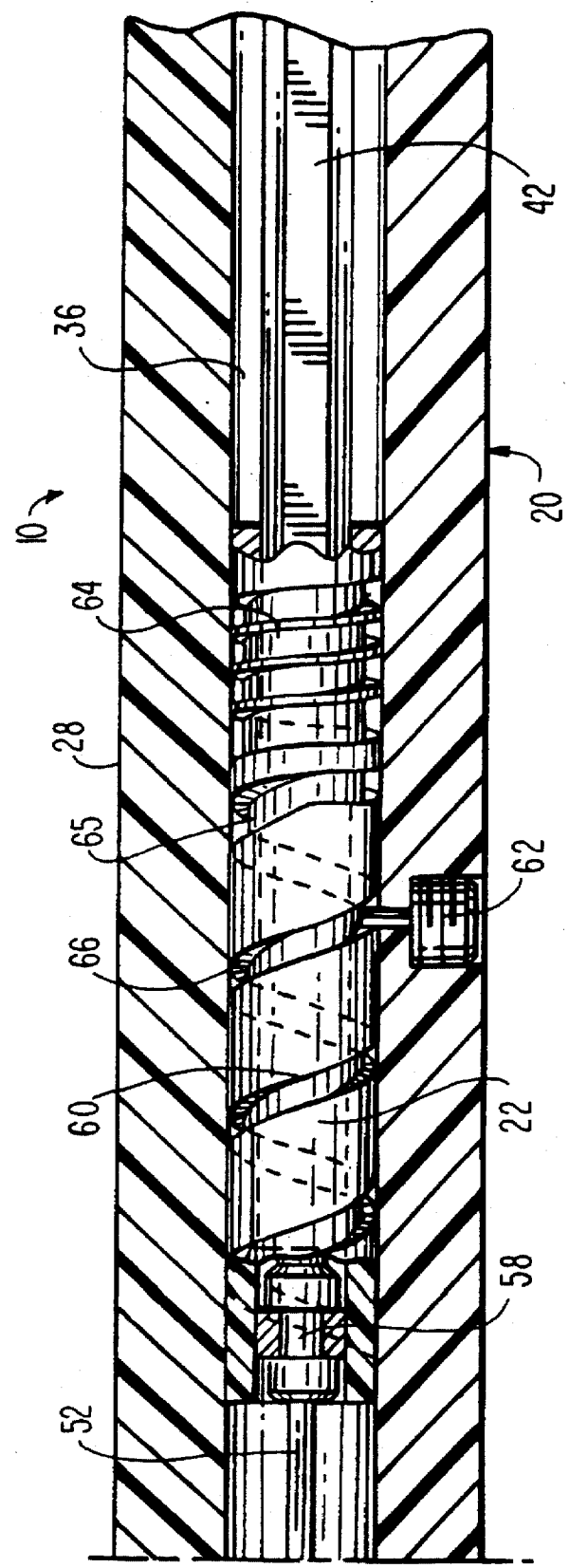

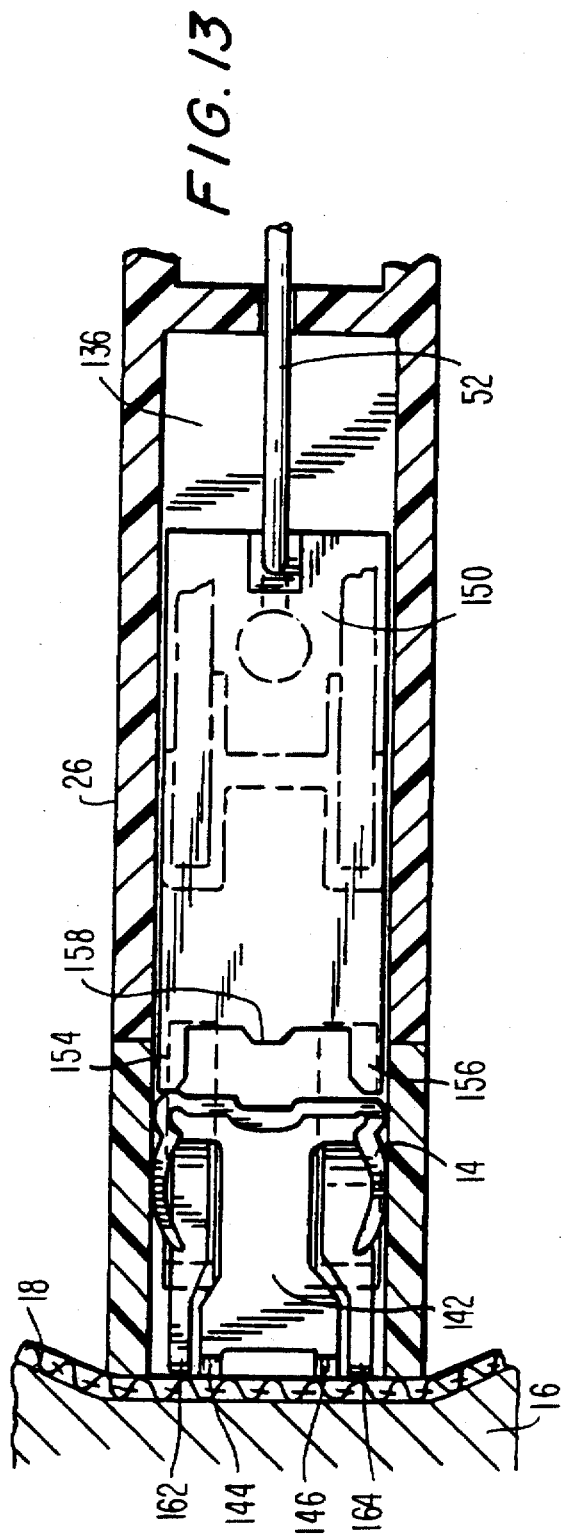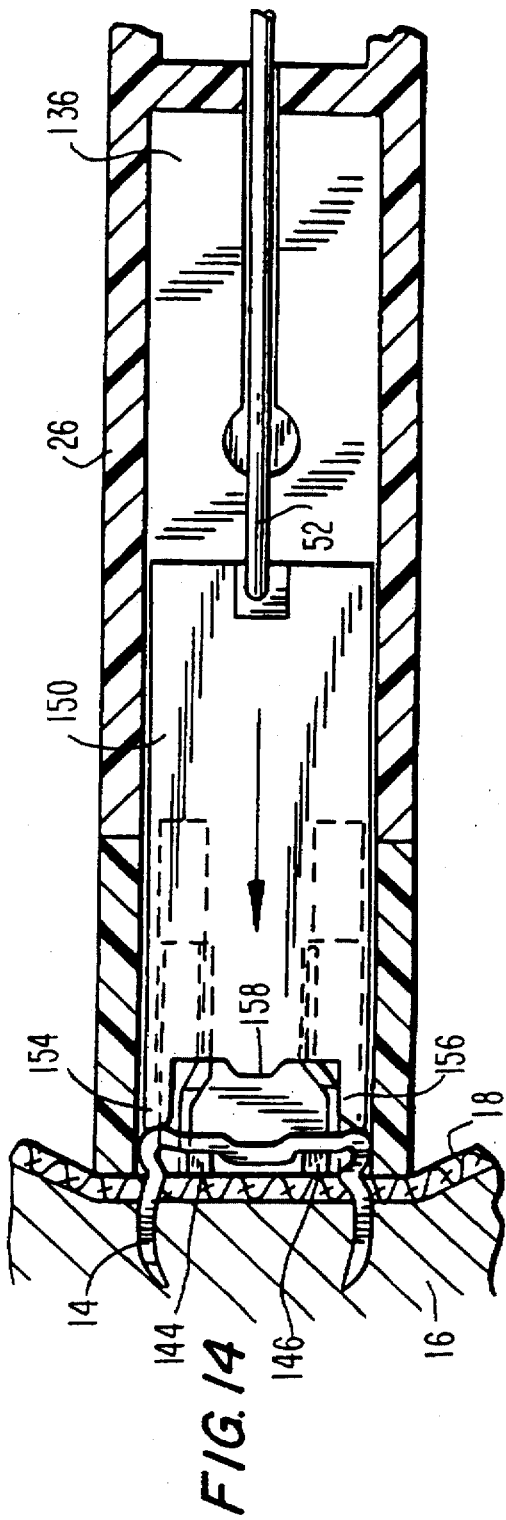

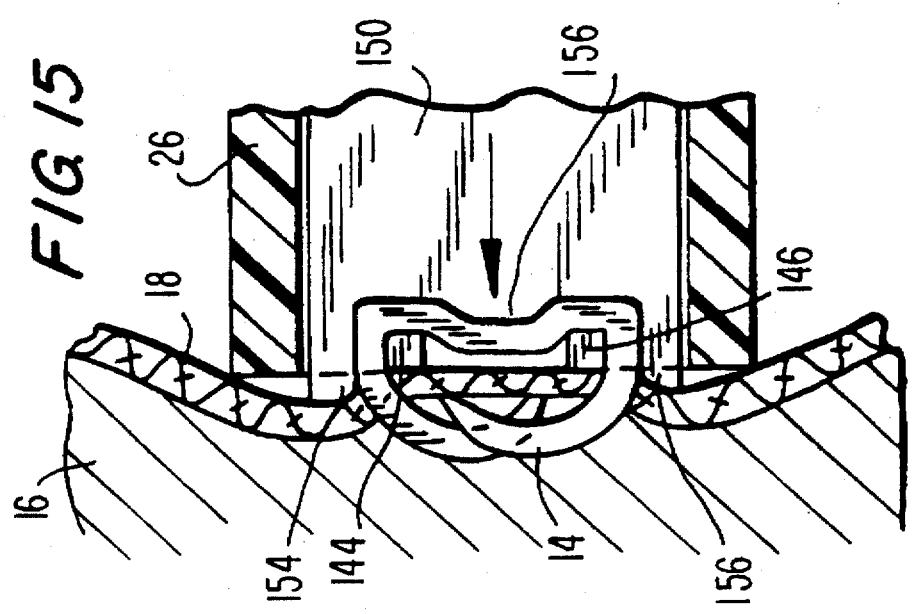
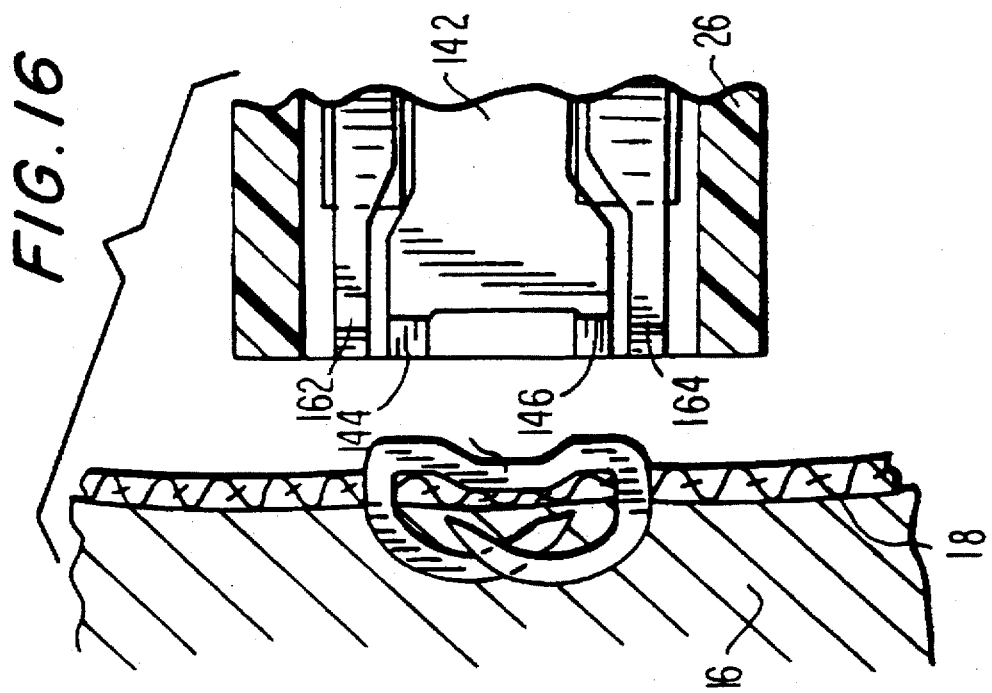

SELF-CONTAINED POWERED SURGICAL APPARATUS

This is a continuation of application Ser. No. 08/238,770, filed on May 5, 1994 now abandoned.

BACKGROUND OF THE INVENTION

1. Field of the Invention

This invention relates to a serf-contained powered surgical apparatus for applying surgical fasteners to body tissue.

2. Description of the Related Art

Hernias may be divided into three general classes: direct hernia, indirect hernia and femoral hernia. In a direct or indirect inguinal hernia, often a pan of the intestine protrudes through a defect in the supporting abdominal wall to form a hernial sac requiring surgery which generally includes a surgical incision in the groin ranging up to six inches in length. Several layers of the abdominal wall are generally separated to reach the herniated portions. During the procedure, the hernia is closed outside the abdominal wall in a manner which resembles the tying of a sack at the neck. Often a surgical mesh is attached by sutures directly over the hernia repaired opening to provide a reinforcement to the opening.

Traditionally, such hernia repairs involved major invasive surgical procedures which often caused excessive trauma to the patient and necessitated unusually long postoperative recuperative periods. In addition, numerous complications, related directly or indirectly to the surgery, often resulted, including bleeding, infection, testicular atrophy, organ damage, nerve damage, blood vessel damage, etc. Furthermore, cutting through the numerous layers of tissue to obtain access to the herniated area often caused severe trauma to the patient.

Invasive surgical procedures have also been utilized in other areas of the body, including surgery on the gall bladder, appendix, lungs and the like. For the reasons previously stated, the use of laparoscopic and endoscopic surgical procedures have been relatively popular and such popularity has provided additional incentive to develop the procedures further.

In laparoscopic procedures, surgery is performed in the interior of the abdomen through a small incision, whereas in endoscopic procedures, surgery is performed in any hollow viscus of the body through narrow endoscopic tubes inserted through small entrance wounds in the skin. Laparoscopic and endoscopic procedures often require the surgeon to act on organs, tissues, and vessels far from the incision, thereby requiring that any instrument used in such procedures be long and slender while being functionally controllable remote from the surgical site. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated.

As noted briefly hereinabove, in hernia surgery, a suitable mesh material is generally sutured over the opening in the tissue. The mesh material is often attached by sutures and left within the opening to act as a reinforcing agent for tissue regrowth. Examples of mesh materials currently utilized in hernia surgery include a polypropylene material marketed by United States Surgical Corporation under the trademark SURGIPRO, and a trifluoroethylene material marketed by W. L. Gore & Associates, Newark, Del., under the trademark GORE-TEX.

With the advent of laparoscopic surgery, the need for suitable mesh attachment techniques performable through a relatively narrow endoscopic tube or cannula has been clearly defined. One example of an instrument which is used in laparoscopic hernia procedures is disclosed in U.S. Pat. No. 5,289,963.

Surgeons have also recognized the benefit of surgical instruments that are actuable with only a limited degree of physical force. Self-powered surgical instruments have been provided to serve these needs and include both gas powered surgical instruments as described, for example, in U.S. Pat. Nos. 3,815,476 and 3,837,555, and electrically powered surgical instruments as described, for example, in U.S. Pat. Nos. 4,635,638 and 5,258,007, and European Patent Application No. 0 552 050. In general, prior an electrically powered surgical instruments have been driven by external power sources. The instruments were connected to the power sources by conductive cables. Such cables could, however, become entangled during a surgical procedure, thereby complicating the operation.

It would be beneficial to provide a serf-contained powered surgical apparatus for applying staples to body tissue to approximate tissue and to attach surgical mesh to body tissue. Such an apparatus should be compact, lightweight and easy to manufacture. Currently, surgical instruments are designed for use in either open, i.e. invasive procedures or endoseopic/laparoscopic procedures. As noted above, endoscopic instruments require elongated shafts to access remote surgical sites. Conventional surgical instruments are not constructed in this manner. It would be advantageous to provide a powered surgical instrument which can be readily adapted for use in laparoscopic or endoseopic procedures as well as conventional surgical procedures.

SUMMARY OF THE INVENTION

The subject invention is directed to a unique self-contained powered surgical apparatus for applying surgical fasteners to body tissue. The apparatus comprises an elongate body defining a longitudinal axis and housing a plurality of surgical fasteners, and a fastener applying assembly operatively associated with a distal end portion of the elongate body. The fastener applying assembly includes an anvil for forming a surgical fastener driven thereagainst and a fastener pusher for driving a surgical fastener toward the anvil. The apparatus further comprises a motor assembly disposed within the elongate body and configured to actuate the fastener pusher to drive a surgical fastener distally toward the anvil to be formed thereby and fastened to body tissue. A power supply is disposed within the elongate body for energizing the motor assembly.

Preferably, an actuating mechanism is driven by the motor assembly for actuating the fastener pusher and includes an axial drive screw formed with a helical thread. The helical thread may define distal, medial and proximal thread sections each having a distinct pitch. The proximal thread section of the axial drive screw has a greater pitch than the distal thread section and effects a fastener forming stroke during use, while the distal thread section of the drive screw effects a fastener advancing stroke. The medial thread section serves as a transition area. Preferably, the actuating mechanism further comprises a fixed thrust pin positioned within the elongate body for interacting with the helical thread of the axial drive screw to effectuate the longitudinal translation thereof. Means are also provided for selectively controlling the motor assembly to operate the surgical apparatus of the subject invention.

In one embodiment of the subject invention, the apparatus is readily adapted for use in conventional and laparoscopic procedures. In particular, the apparatus includes an elongate extension shaft configured to engage the proximal end portion of the elongate body. Once engaged, the extension shaft facilitates utilization of the apparatus in laparoscopic surgical procedures wherein access to the surgical site is limited to a small incision formed in the patient's abdominal wall. Preferably, the extension shaft includes means for interacting with the motor controlling means at the proximal end of the elongate body to effectuate remote operation of the apparatus.

In the illustrated embodiment of the powered surgical apparatus of the subject invention, a fastener carrying cartridge is operatively associated with a distal end portion of the elongate body. The cartridge preferably contains a plurality of staples and is configured as a replaceable unit. In such an embodiment, the anvil forms a surgical fastener driven theretoward and a pusher mechanism is provided which is driven by the motor assembly for driving a surgical fastener toward the anvil to be formed thereby and fastened to body tissue.

Further features of the self-contained powered surgical stapling apparatus of the subject invention will become more readily apparent to those having ordinary skill in the art from the following detailed description of preferred embodiments of the invention taken in conjunction with the drawings.

BRIEF DESCRIPTION OF THE DRAWINGS

So that those skilled in the art to which the subject invention appertains will more readily understand how to make and use the powered surgical stapling apparatus of the subject invention, preferred embodiments of the apparatus will be described in detail hereinbelow with reference to the drawings wherein:

FIG. 1 is a perspective view of the self-contained powered surgical apparatus of the subject invention applying a plurality of surgical fasteners to body tissue during a conventional invasive surgical procedure;

FIGS. 1A and 1B are perspective views of the self-contained powered surgical stapling apparatus of FIG. 1, respectively, showing a flexible and a rigid elongate extension shaft connected to the proximal end to facilitate utilization of the apparatus during an endoscopic surgical procedure wherein, for example, a surgical mesh is attached to body tissue;

FIG. 2 is a perspective view of a mechanical hand configured to extend through a trocar or cannula device during laparoscopic surgery to operate the powered surgical stapling apparatus of the subject invention;

FIG. 8 is a cross-sectional view taken along line 8—8 of FIG. 6 illustrating the connective interaction between the axial drive screw and the firing rod;

FIG. 9 is a cross-sectional view taken along line 9—9 of FIG. 6 illustrating the operative interaction between the helical thread of the drive screw and the stationary thrust pin which effects its movement;

FIG. 10 is a cross-sectional view taken along line 10—10 of FIG. 7 illustrating the control mechanism of the surgical apparatus of FIG. 1;

FIG. 11 is a side elevational view in cross-section of a medial portion of the apparatus of FIG. 1 with the axial drive screw partially advanced in a distal direction;

FIG. 13 is a plan view in cross-section of the fastener applying assembly of the surgical apparatus of FIG. 1 with the pusher plate in a proximal position prior to actuation of the apparatus;

FIG. 14 is a plan view in cross-section of the fastener applying assembly of the surgical apparatus of FIG. 1 with the pusher plate advanced in a distal direction to drive a surgical fastener toward the anvil, through surgical mesh, and into body tissue;

FIG. 15 is a plan view in cross-section of the distal-most portion of the fastener applying assembly of the surgical apparatus of FIG. 1 with a surgical fastener being formed against the anvil; and FIG. 16 is a plan view in cross-section of the distal-most portion of the fastener applying assembly of the surgical apparatus of FIG. 1 with a fully formed surgical fastener released from the apparatus to attach surgical mesh to body tissue.

DETAILED DESCRIPTION OF THE PREFERRED EMBODIMENT

Figure 1B:
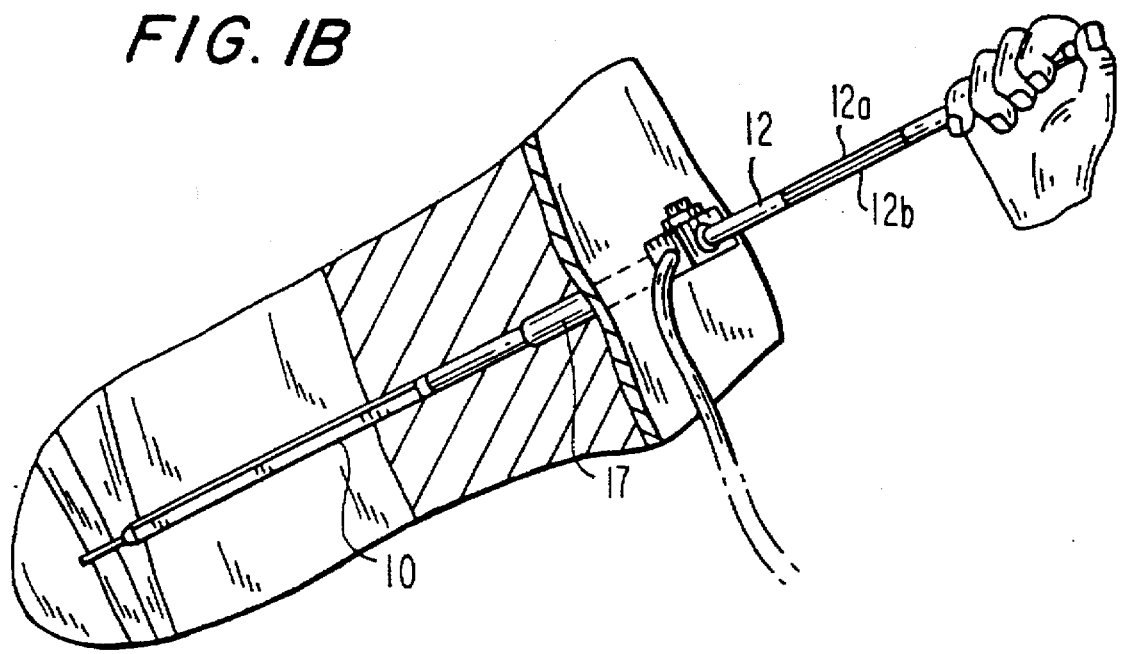

In the drawings and in the description which follows, the term "proximal", as is traditional, will refer to the end of the apparatus which is closest to the operator, while the term "distal" will refer to the end which is furthest from the operator.

The present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic robe. To the contrary, it is believed that the present invention may find use in procedures wherein access is limited to a small incision including but not limited to arthroscopic and/or laparoscopic procedures.

Referring now to the drawings wherein like reference numerals identify similar structural elements of the subject invention, there is illustrated in FIG. 1 a self-contained powered surgical apparatus constructed in accordance with a preferred embodiment of the subject invention and designated generally by reference numeral 10.

Referring to FIG. 1, powered surgical apparatus 10 is configured for use as a hand-held device for applying surgical fasteners to body tissue during conventional invasive surgical procedures. By way of example only, surgical apparatus 10 may have a length measuring from about 5.0 inches to about 7.0 inches, and an outer diameter ranging from about 0.450 inches to about 0.500 inches. Preferably, the length of surgical apparatus 10 is between 6.0 inches and 6.5 inches, while the preferred diameter is between 0.470 inches and 0.480 inches. Clearly, other dimensions are contemplated. In one embodiment of the subject invention, surgical apparatus 10 is also adapted for use in endoscopic procedures through remote actuation from a location outside the patient's body, as shown in FIGS. 1A and 1B. This is achieved by providing an elongated extension shaft 12 which attaches to the proximal end of surgical apparatus 10 by commonly known connective methods such as a snap fit. Extension shaft 12 is preferably dimensioned and configured for insertion through a cannula or trocar device and has a length measuring from about 10.0 to 12.0 inches. A flexible shaft 12' or rigid shaft 12 can be utilized.

Referring to FIG. 2, in another preferred embodiment of the subject invention, surgical apparatus 10 is intended to be operated by a mechanical hand 15 which is configured to extend through a trocar or cannula device during a laparoscopic surgical procedure. Mechanical hand 15 includes four articulated digits 15a–15d and an opposable thumb 15e which are hinged together to enable relative movement between a narrow constricted position to extend through trocar 17 and a deployed or spread position to perform dexterous tasks such as operating surgical apparatus 10 by actuating a switch provided on the apparatus.

Referring to FIG. 1A, surgical apparatus 10 is preferably configured to apply a plurality of surgical staples 14 to body tissue 16 in such a manner so as to attach a surgical mesh 18 to the body tissue to reinforce a surgical repair thereof, such as, for example, during a hernia repair procedure. Surgical apparatus 10 is also configured to apply surgical fasteners to body tissue to approximate tissue or close wounds as shown in FIG. 1.

Figure 3:
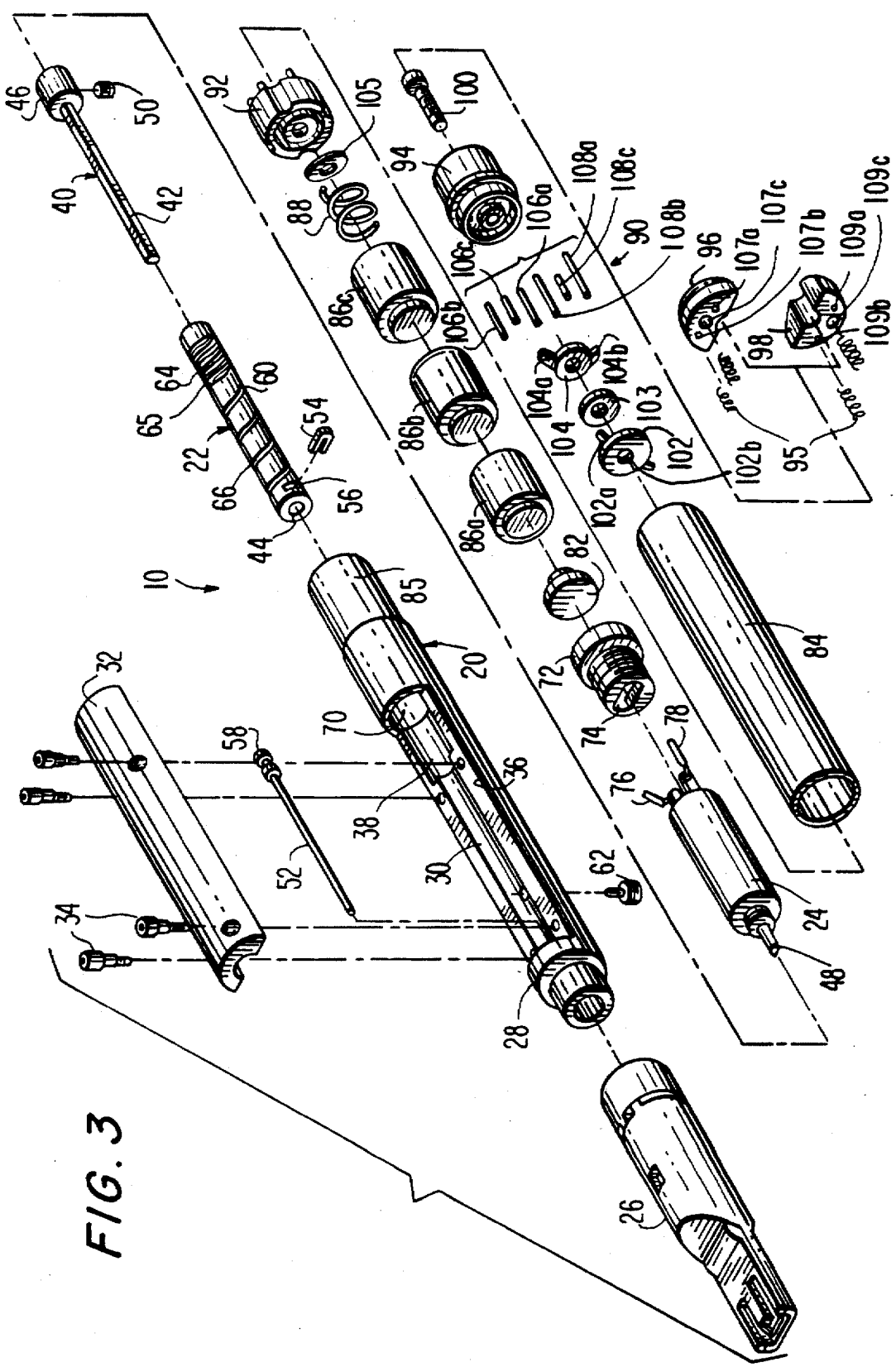
FIG. 3 is an exploded perspective view of the self-contained powered surgical apparatus illustrated in FIG. 1.

Referring to FIG. 3, surgical apparatus 10 comprises an elongate body 20 defining a longitudinal axis and housing an axial drive screw 22 and a motor assembly 24. In addition, a fastener applying assembly 26 is disposed at the distal end of elongate body 20. The elongate body 20 includes a main body portion 28 having a stepped cylindrical bore 30 formed therein and a removable cover assembly 32 attached thereto by threaded fasteners 34. Cylindrical bore 30 defines a distal section 36 dimensioned and configured to accommodate axial drive screw 22 and a proximal section 38 dimensioned and configured to accommodate a drive rod 40.

Drive rod 40 includes an elongated shaft portion 42 having a polygonal cross-sectional configuration adapted for engagement within a correspondingly configured bore 44 which extends through the axial drive screw 22. Drive rod 40 further includes a mounting portion 46 configured to engage the drive shaft 48 of motor assembly 24. A set screw 50 is provided to effect the secured engagement between drive rod 40 and drive shaft 48. Thus, when the motor assembly 24 is operating, rotation of drive shaft 48 will be directly translated to drive rod 40, and in turn, to the axial drive screw 22.

Axial drive screw 22 is further engaged to a push rod 52 at the distal end thereof. A generally C-shaped mounting clip 54 is provided to facilitate this engagement. Mounting clip 54 is accommodated within a transverse slot 56 defined adjacent the distal end of drive screw 22 and engages a flange 58 formed at the proximal end of push rod 52, as best seen in FIG. 8. Push rod 52 extends to the fastener applying assembly 26 and interacts therewith to effectuate the application of surgical fasteners to body tissue during utilization of the apparatus. This interaction will be described in greater detail below with reference to FIGS. 4 and 5.

With continued reference to FIG. 3 in conjunction with FIG. 9, axial drive screw 22 includes a helical thread 60 which is operatively associated with a stationary thrust pin 62 provided in main body portion 28. Thrust pin 62 effectuates the longitudinal translation of the axial drive screw 22 during operation of the apparatus. Helical thread 60 defines a proximal thread section 64, a medial thread section 65, and a distal thread section 66. The proximal thread section 64 has a greater pitch than the distal section 66. Thus, in operation, when the axial drive screw 22 is rotated relative to the thrust pin 62, a greater degree of longitudinally directed force will be imparted by the drive screw 22 during its interaction with the proximal thread section 64 than during its interaction with the distal thread section 66. In use, this interaction corresponds to particular periods of the fastener applying operation. In particular, the interaction between the drive screw 22 and thrust pin 62 within distal thread section 66 corresponds to a fastener advancing stroke while the interaction between the drive screw 22 and thrust pin 62 within proximal thread section 64 corresponds to a fastener forming stroke (see generally, FIGS. 13–15). The medial thread section 65 is defined between the distal and proximal/thread sections of drive screw 22 as a transition area.

Figure 7:
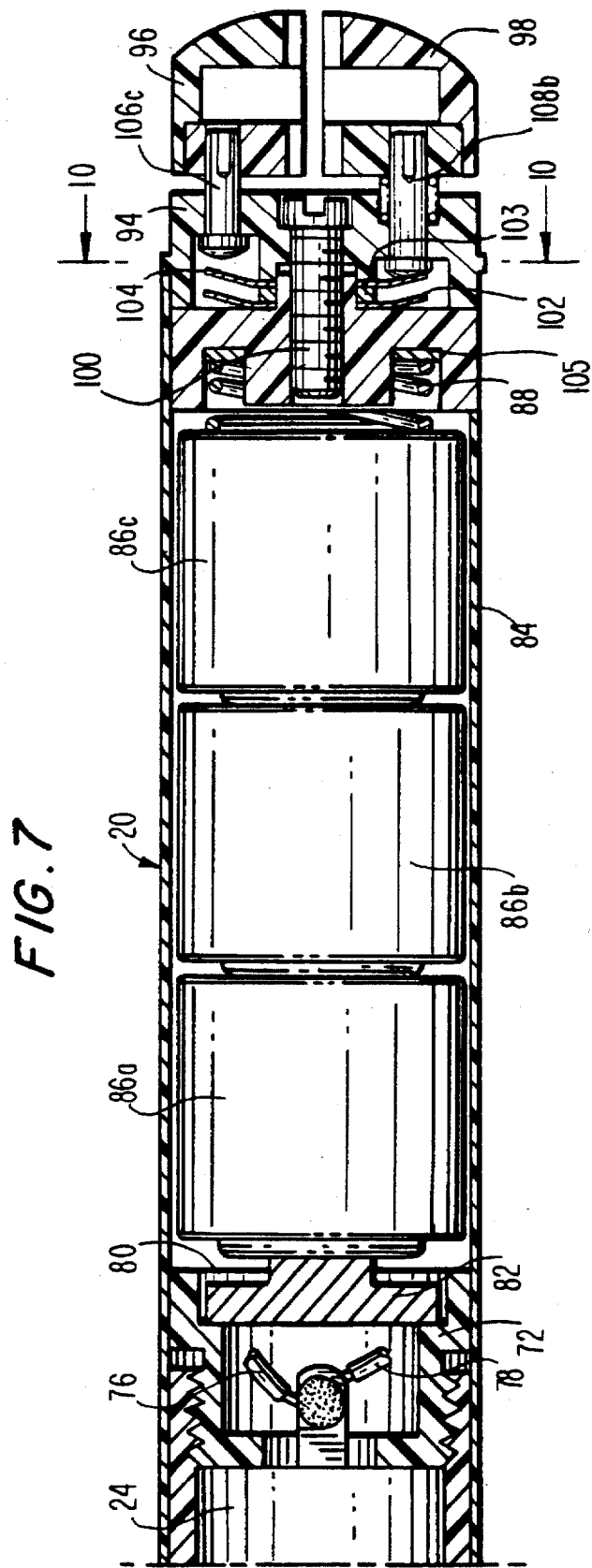
FIG. 7 is a side elevational view in cross-section of the proximal portion of the surgical apparatus of FIG. 1 illustrating the internal power cells and the switching mechanism for selectively controlling the operation of the apparatus.

The main body portion 28 of surgical apparatus 10 further defines a proximal/ chamber 70 configured to accommodate motor assembly 24, and a threaded fitting 72 is provided to retain motor assembly 24 therein. Fitting 72 is formed within a channel 74 to accommodate the positive and negative terminals 76 and 78 of motor assembly 24, and an annular seat 80 is provided to accommodate an electrical transfer plate 82 (see FIG. 7).

The elongate body 20 of surgical apparatus 10 further includes a substantially cylindrical housing portion 84 which mounts to the reduced proximal end section 85 of main body portion 28. With continued reference to FIG. 3 in conjunction with FIG. 7, housing portion 84 encloses a plurality of power storage cells 86a–86c, preferrably replaceable, which energize the motor assembly 24 to effect its operation. The power cells may be rechargeable such as nickel-cadmium type batteries, standard alkaline type batteries or lithium batteries. Power cells 86a–86c are biased in a distal direction toward transfer plate 82 by a coiled compression spring 88.

Powered surgical apparatus 10 further includes a switching assembly 90 for selectively controlling the operation of motor assembly 24 and hence the actuation of the fastener applying assembly 26. Switching assembly 90 includes distal and proximal switch housings 92 and 94, and right and left actuation buttons 96 and 98 for respectively effecting proximal and distal translation of drive screw 22. A plurality of coiled springs 95 bias actuation buttons 96 and 98 in a proximal direction. Switch housings 92 and 94 are mounted to one another and fastened to the proximal end of surgical apparatus 10 by a threaded connector 100, and are operatively separated from one another by a distal contact plate 102, a medial insulating ring 103, a proximal contact plate 104. A proximal contact ring 105 is disposed between proximal switch housing 92 and compression spring 88.

Distal contact plate 102 includes a pair of opposed upturned contact tabs 102a and 102b, and proximal contact plate 104 includes a pair of opposed upturned contact tabs 104a and 104b which are positioned approximately 60° out of phase with tabs 102a and 102b. Each actuation button has associated therewith three contact pins, two of which interact with contact plates 102 and 104 to control the relative movement of drive screw 22. In particular, actuation button 96 includes two long pins 106a and 106b and one short pin 106c. Short pin 106c is seated within a central reception port 107c, while long pins 106a and 106b are seated within lateral reception ports 107a and 107b. Long pin 106a and short pin 106c are positioned to selectively engage contact tabs 102a and 104a, respectively, while long pin 106b remains free from electrical contact. Similarly, actuation button 98 includes long pins 108a and 108b, and short pin 108c. Short pin 108c is seated within a central reception port 109c, while long pins 108a and 108b are seated within lateral reception ports 109a and 109b. Long pin 108b and short pin 108c are positioned to selectively engage contact tabs 102b and 104b respectively, while long pin 108a remains free from electrical contact.

Figure 7A:
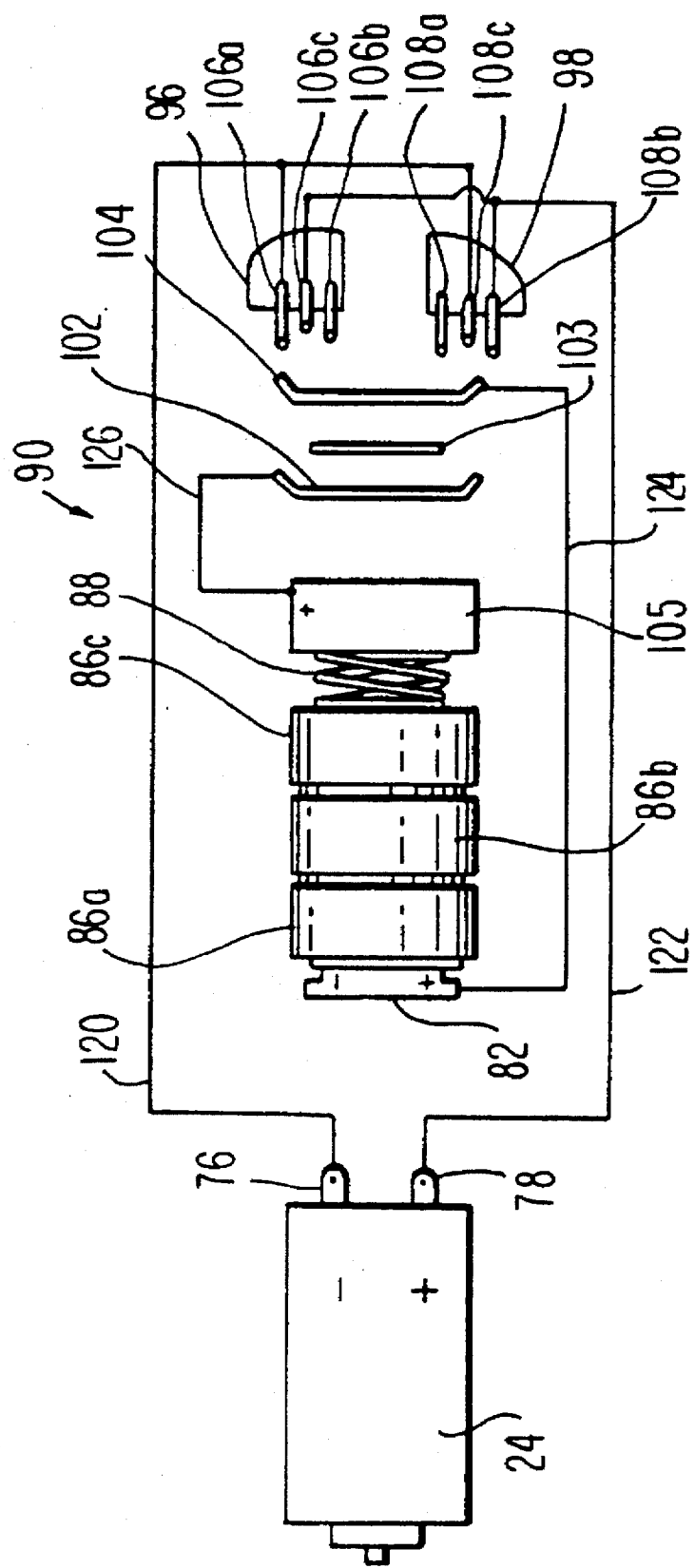
FIG. 7A is a schematic representation of the switching mechanism for selectively controlling the operation of the surgical apparatus of FIG. 1.

The wiring configuration of switching assembly 90 is depicted in FIG. 7A and includes a motor line 120 which interconnects the positive terminal 76 of motor assembly 24 to contact pins 106a and 108c, and a motor line 122 which interconnects the negative terminal 78 of motor assembly 24 to contact pins 106c and 108b. In addition, a transmission line 124 extends between electrical transfer plate 82 and contact plate 104, and a transmission line 126 interconnects contact plate 102 and contact ring 105.

In use, when actuation button 98 is depressed, long pin 108b contacts tab 102b distal contact plate 102 and short pin 108c contacts tab 104b of proximal contact plate 104. Thus, the positive terminals of power cells 86a–86c will be connected to the negative terminal 78 of motor assembly 84 and the negative terminals of power cells 86a–86c will be connected to the positive terminal 76 of motor assembly 84, causing drive shaft 48 to rotate in a clockwise direction to move the axial drive screw 22 in a distal direction. When actuation button 96 is depressed, long pin 106a contacts tab 102a of distal contact plate 102 and short pin 106c contacts tab 104a proximal contact plate 104. Thus, the positive terminals of power cells 86a–86c will be connected to the positive terminal 76 of motor assembly 24 and the negative terminals of power cells 86a–86c will be connected to the negative terminal 78 of motor assembly 84, causing drive shaft 48 to rotate in a counter-clockwise direction to move the axial drive screw 22 in a proximal direction. It is also envisioned that a single actuator button can be provided which will be actuable to operate an axial drive screw having a reverse thread formed therein. The reverse thread will cause a distally translating drive screw to automatically translate in a proximal direction at the conclusion of a fastener forming stroke.

As discussed briefly hereinabove, surgical apparatus 10 is preferably designed for insertion through a trocar or cannula device to apply fasteners within a body cavity while being actuable remote from the surgical site. Shaft 12 includes elongate transmission members 12a and 12b (or 12a' and 12b') for effectuating remote actuation of switching assembly 90 (see FIGS. 1A and 1B). Transmission members 12a and 12b (or 12a' and 12b') may comprise a pair of substantially rigid rods for transmitting a mechanical signal to actuation buttons 96 and 98, or, in the alternative, the transmission members may comprise transmission cables for directing an electrical signal to switching assembly 90. In either instance, the shaft would include two actuation buttons to respectively actuate buttons 96 and 98 to cause the translation of drive screw 22 in proximal and distal directions as described above.

As noted above, surgical apparatus 10 can also preferably be configured to be used in laparoscopic procedures without the extension shaft 12 by employing the mechanical hand illustrated in FIG. 2. Due to the simple actuation features of the subject invention, e.g. push button actuation, the articulated fingers of mechanical hand 15 can be easily manipulated to operate the instrument and perform a surgical task.

Figure 4:
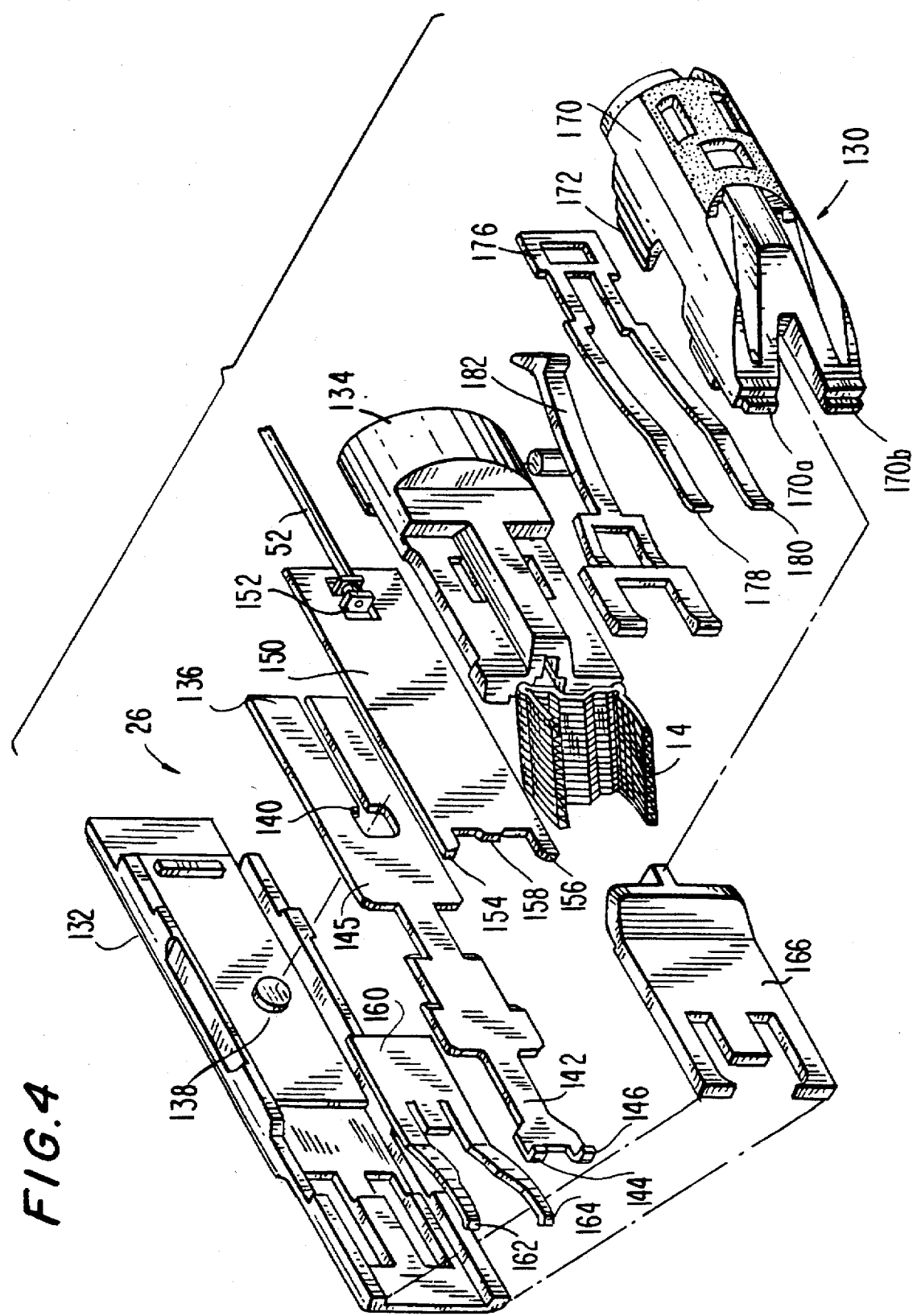
FIG. 4 is an exploded perspective view of the fastener applying assembly of the surgical apparatus of FIG. 1 including the fastener carrying cartridge.
Figure 5:
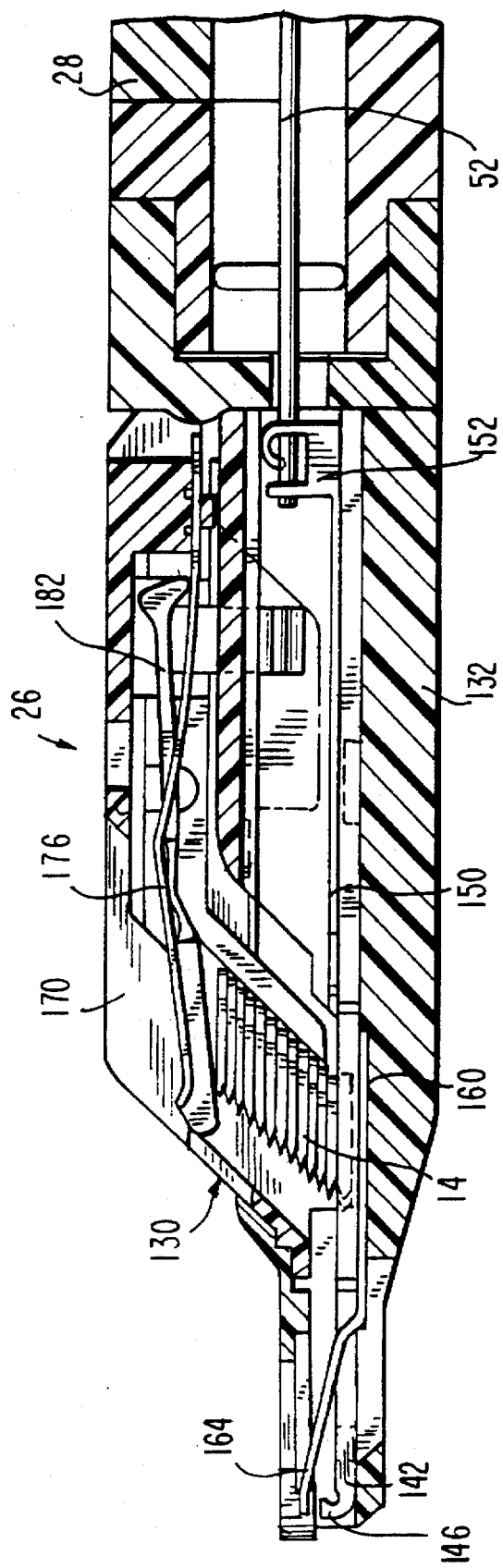
FIG. 5 is a side elevational view in cross-section of the distal portion of the powered surgical apparatus of FIG. 1 with the fastener cartridge carrying a complete array of surgical fasteners prior to utilization.
Figure 6:
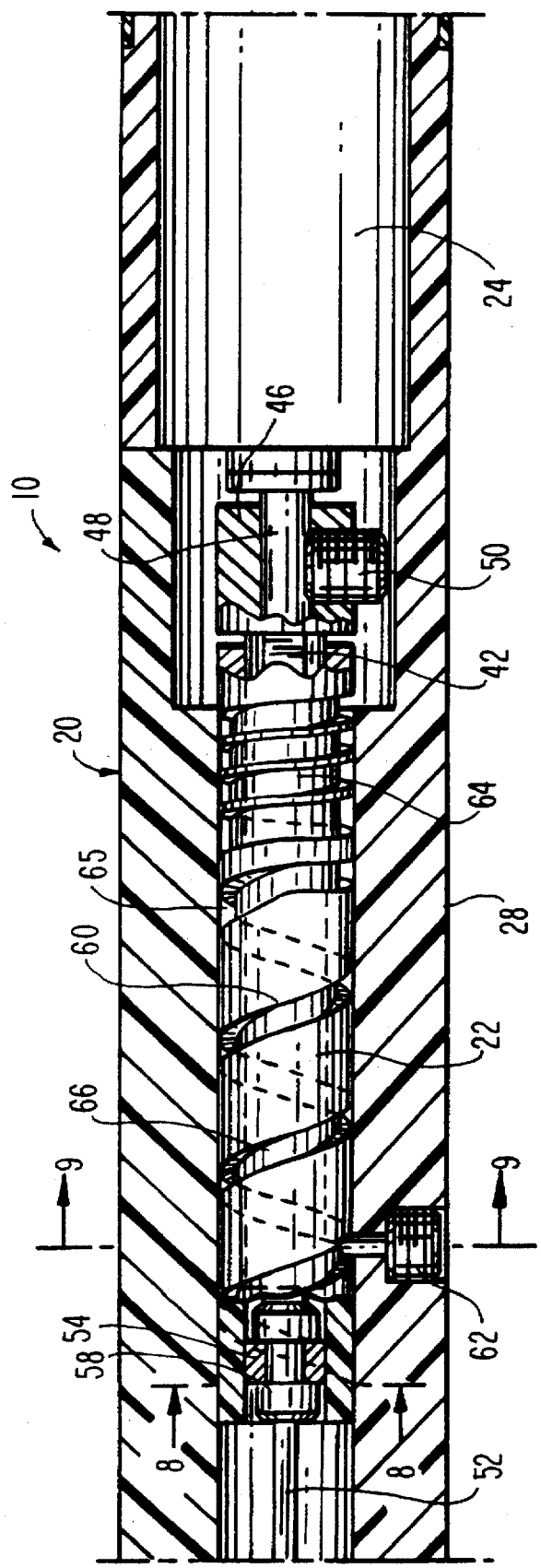
FIG. 6 is a side elevational view in cross-section of the medial portion of the powered surgical apparatus of FIG. 1 with the axial drive screw in a proximal position prior to actuation.

Referring to FIGS. 4 and 5, there is illustrated the fastener applying assembly 26 of the subject invention including the fastener containing cartridge 130 which houses a plurality of surgical staples 14 that are particularly shaped to penetrate and attach surgical mesh to body tissue. In one embodiment, the cartridge is removably mounted to the apparatus so it can be replaced with a fresh cartridge.

As illustrated in FIG. 4, fastener applying assembly 26 includes opposed housing portions 132 and 134 which are configured for connective engagement. A substantially planar anvil plate 136 is mounted to housing portion 132 through the engagement of a projection 138 on housing portion 132 and a corresponding aperture 140 in anvil plate 136. The fastener forming portion 142 of anvil plate 136 extends distally from the main body portion 145 thereof and includes a pair of spaced apart upturned anvil feet 144 and 146 against which surgical staples 14 are driven to be formed.

Fastener applying assembly 26 further includes a substantially planar pusher plate 150. Pusher plate 150 is provided with a collar 152 at the proximal end thereof for engaging the distal end of pusher rod 52. The distal end portion of pusher plate 150 is formed with a pair of opposed distally extending staple advancers 154 and 156 and a central staple stabilizer 158. In use, when push rod 52 is driven in a distal direction by axial drive screw 22, pusher plate 150 translates distally, urging the distal-most staple 14 toward anvil feet 144 and 146 to be formed thereby and applied to the body tissue.

Fastener applying assembly 26 further comprises staple ejector spring 160 which includes a pair of spaced apart resilient ejector legs 162 and 164. Ejector spring 160 is adapted to eject a staple from anvil plate 136 after the staple has been formed thereby. In use, when pusher plate 150 is in a distal position, ejector legs 162 and 164 of ejector spring 160 are maintained in a deflected position. As pusher plate 150 returns to a proximal position after a staple has been formed by anvil feet 144 and 146, ejector legs 162 and 164 are permitted to assume their normally biased position. As a result, the formed staple is released from anvil feet 144 and 146 and ejected from the fastener applying assembly 26. A cover member 166 is provided for enclosing the fastener forming area defined by the distal portion 142 of anvil plate 136.

The fastener cartridge 130 of fastener applying assembly 26 includes a removable cartridge housing 170 including deflectable lateral tabs 172 and 174 for releasably engaging the outer surfaces of housing portion 134. Cartridge housing 170 also includes a pair of distal feet 170a and 170b which are configured to slide beneath cover member 166 to secure the cartridge housing 170. Disposed within the cartridge housing 170 is a retainer spring 176 having opposed elongated legs 178 and 180, and a pivoting staple follower 182. The staple follower 182 and retainer spring 176 serve to maintain the staple stack in an angular configuration and progressively feed the staple stack from the cartridge housing 170 into the fastener forming area as they are ejected from the fastener applying assembly 26.

Referring now to FIGS. 6 and 11–15, the operation of powered surgical apparatus 10 will be described through illustrating a fastener applying procedure wherein surgical mesh 18 is attached to body tissue 16. Initially, the fastener applying assembly 26 is directed toward the surgical site as illustrated in FIG. 13. At such a time, pusher plate 150 is disposed in the proximal-most position behind a distal-most staple 14 (or bottom-most), and the axial drive screw 22 is in the proximal-most position illustrated in FIG. 6. Depression of the actuator button 98 of switching assembly 90 causes the axial drive screw 22 to translate in a distal direction as helical thread 60 interacts with thrust pin 62, as illustrated in FIG. 11. During this initial period of distal translation, the distal thread section 66 of helical thread 60 is in contact with thrust pin 62. This interaction corresponds to the fastener driving stroke illustrated in FIG. 14, wherein staple 14 is driven through surgical mesh 18 and into body tissue 16 by pusher plate 150, but not yet formed.

Figure 12:
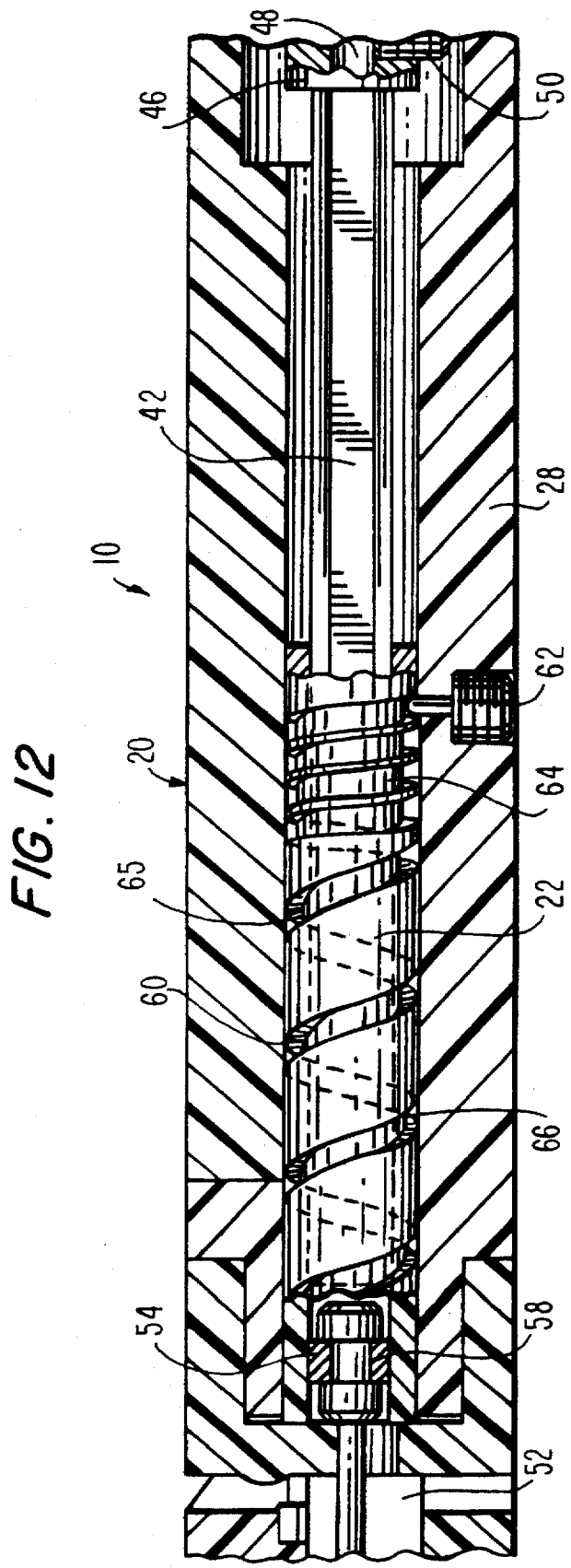
FIG. 12 is a side elevational view in cross-section of a medial portion of the apparatus of FIG. 1 with the axial drive screw advanced to a distal-most position.

Continued distal translation of axial drive screw 22 results in the interaction of thrust pin 62 and the proximal thread section 64 of helical thread 60, as best seen in FIG. 12. This interaction corresponds to the fastener forming stroke illustrated in FIG. 15, and generates a substantial axial force which is exerted by the pusher plate 150 to form staple 14 against the anvil feet 144 and 146 of anvil plate 136. After the staple has been properly formed in such a manner so as to secure surgical mesh 18 to body tissue 16, actuation button 96 may be depressed by the user to reverse the direction of the drive shaft 48 of motor assembly 24, thereby causing axial drive screw 22 to translate in a proximal direction, drawing therewith pusher plate 150. At such a time, staple ejector spring 160 will urge the formed staple from the fastener applying assembly 26 as illustrated in FIG. 16, and the apparatus may be withdrawn from the site of application and reoriented for further staple applications.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A self-contained powered surgical apparatus for applying surgical fasteners to body tissue comprising:
    a) an elongate body defining a longitudinal axis and housing a plurality of surgical fasteners;
    b) a stationary anvil positioned at a distal end of the elongate body for forming a surgical fastener;
    c) a fastener pusher for individually driving the surgical fasteners housed within the elongate body in a distal direction toward the anvil;
    d) a motor assembly disposed within the elongate body and configured to actuate the fastener pusher to drive a surgical fastener toward the anvil;
    e) an axial drive screw driven by the motor assembly and mounted to translate within the elongate body in a longitudinal direction; and
    f) a power source disposed within the elongate body for energizing the motor assembly.

2. A powered surgical apparatus as recited in claim 1, wherein the axial drive screw is formed with a helical thread defining a distal threaded portion having a first pitch and a proximal threaded portion having a second pitch.

3. A powered surgical apparatus as recited in claim 2, wherein the proximal threaded portion has a greater pitch than the distal threaded portion, the distal threaded portion effecting a fastener driving stroke and the distal threaded portion effecting a fastener forming stroke.

4. A powered surgical apparatus as recited in claim 2, further comprising a stationary thrust pin positioned within the elongate body for interacting with the helical thread of the axial drive screw to effectuate longitudinal translation thereof.

5. A powered surgical apparatus as recited in claim 1, further comprising an actuator associated with a proximal end of the elongate body for selectively controlling the motor assembly to operate the apparatus.

6. A powered surgical apparatus as recited in claim 5, wherein the actuator includes first and second actuator buttons for respectively controlling proximal and distal translation of the fastener pusher.

7. A powered surgical apparatus as recited in claim 6, further comprising an elongate extension shaft configured to engage the proximal end portion of the elongate body to facilitate utilization of the apparatus during an endoscopic surgical procedure.

8. A powered surgical apparatus as recited in claim 7, wherein the elongate extension shaft includes means for interacting with the actuator to effectuate remote operation of the motor assembly.

9. A powered surgical apparatus as recited in claim 8, wherein the means for interacting with the actuator comprises fast and second elongated control rods configured to respectively interact with the first and second.

10. A powered surgical apparatus as recited in claim 1, wherein the elongate body includes a detachable cartridge portion configured to house a plurality of surgical fasteners.

11. A powered surgical apparatus as recited in claim 1, wherein the elongate body has a substantially uniform outer diameter.

12. A powered surgical apparatus as recited in claim 1, wherein the elongate body has an operative length from about 6.0 inches to about 6.5 inches.

13. A powered surgical apparatus as recited in claim 1 wherein the anvil includes a pair of spaced apart upturned fastener forming feet.

14. A surgical apparatus as recited in claim 1, wherein the fastener pusher comprises an elongate drive plate including a pair of spaced apart distally extending fastener engaging fingers.

15. A self-contained powered surgical apparatus for applying surgical fasteners to body tissue comprising:
    a) an elongate body defining a longitudinal axis and having a cartridge housing a plurality of surgical fasteners;
    b) means fixedly positioned at a distal end of the elongate body for forming a surgical fastener;
    c) means for individually driving the surgical fasteners housed within the elongate body in a distal direction toward the fastener forming means;
    d) a motor assembly disposed within the elongate body;
    e) an axial drive screw driven by the motor assembly and mounted to translate within the elongate body in a longitudinal direction for actuating the fastener driving means to individually drive surgical fasteners toward the fastener forming means; and
    f) a power supply disposed within the elongate body for energizing the motor assembly.

16. A powered surgical apparatus as recited in claim 15, wherein the fastener forming means comprises an anvil including a pair of spaced apart upturned fastener forming feet.

17. A powered surgical apparatus as recited in claim 15, wherein the fastener driving means comprises an elongate drive plate including a pair of spaced apart distally extending fastener engaging fingers.

18. A powered surgical apparatus as recited in claim 15, wherein the axial drive screw is formed with a helical thread defining a distal threaded portion having a first pitch and a proximal threaded portion having a second pitch.

19. A powered surgical apparatus as recited in claim 18, wherein the proximal threaded portion has a greater pitch than the distal threaded portion, the distal threaded portion effecting a fastener driving stroke and the distal threaded portion effecting a fastener forming stroke.

20. A powered surgical apparatus as recited in claim 18, further comprising a stationary thrust pin positioned within the elongate body for interacting with the helical thread of the axial drive screw to effectuate the longitudinal translation thereof.

21. A powered surgical apparatus as recited in claim 15, further comprising a control mechanism associated with a proximal end of the elongate body for selectively controlling the motor assembly to operate the apparatus.

22. A power surgical apparatus as recited in claim 15, wherein the elongate body has a substantially uniform outer diameter.

* * * * *